US010173100B2

(12) United States Patent
Sinha et al.

(10) Patent No.: US 10,173,100 B2
(45) Date of Patent: *Jan. 8, 2019

(54) SPORT TRAINING EQUIPMENT

(71) Applicants:Navyaa Sinha, San Diego, CA (US);
Aditi Sinha, San Diego, CA (US)

(72) Inventors: Navyaa Sinha, San Diego, CA (US);
Aditi Sinha, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/670,995

(22) Filed: Aug. 7, 2017

(65) Prior Publication Data

US 2018/0001138 A1    Jan. 4, 2018

Related U.S. Application Data

(63) Continuation-in-part of application No. 15/268,538, filed on Sep. 17, 2016, now Pat. No. 9,724,561.

(51) Int. Cl.
| | |
|---|---|
| *G06K 9/00* | (2006.01) |
| *G06T 7/20* | (2017.01) |
| *H04N 5/77* | (2006.01) |
| *A63B 24/00* | (2006.01) |
| *A63B 69/38* | (2006.01) |
| *G09B 19/00* | (2006.01) |
| *H04N 5/225* | (2006.01) |

(Continued)

(52) U.S. Cl.
CPC .......... *A63B 24/0003* (2013.01); *A63B 69/38* (2013.01); *G06K 9/00342* (2013.01); *G06K 9/00724* (2013.01); *G06T 7/20* (2013.01); *G09B 19/0038* (2013.01); *H04N 5/2252* (2013.01); *H04N 5/23241* (2013.01); *H04N 5/772* (2013.01); *H04N 21/2743* (2013.01); *H04N 21/4223* (2013.01); *H04N 21/42202* (2013.01); *H04N 21/4334* (2013.01); *A63B 2220/53* (2013.01); *G06T 2207/30221* (2013.01)

(58) Field of Classification Search
CPC . A63B 24/0003; A63B 2220/53; A63B 69/38; A63B 2225/50; A63B 2220/50; A63B 2220/62; A63B 2220/806; A63B 69/0002; A63B 2220/803; H04N 21/4223; H04N 21/2743; H04N 5/772; H04N 21/4334; H04N 21/42202; G06K 9/00342; G06T 2207/30224; G09B 19/0038
See application file for complete search history.

(56) References Cited

U.S. PATENT DOCUMENTS

| | | | | |
|---|---|---|---|---|
| 5,500,635 | A * | 3/1996 | Mott | A43B 1/0072 310/311 |
| 9,327,177 | B2 * | 5/2016 | Yamamoto | A63B 69/38 |

(Continued)

FOREIGN PATENT DOCUMENTS

| | | | |
|---|---|---|---|
| JP | 2012130414 A | * | 7/2012 |
| JP | 2015107237 A | * | 6/2015 |

*Primary Examiner* — John Villecco

(57) ABSTRACT

A system for recording and analyzing an activity, such as a golf activity, is provided. The system comprises an impact detection device and one or more video capture unit for recording and displaying recorded activities. Preferred activities are saved, and may be viewed at a separate viewing unit located remote from the video capture unit. The remote viewing unit allows for replay and analysis of the saved activities. In addition, saved activities and data may be uploaded to the Internet for later viewing and analysis.

22 Claims, 17 Drawing Sheets

(51) Int. Cl.
*H04N 5/232* (2006.01)
*H04N 21/422* (2011.01)
*H04N 21/433* (2011.01)
*H04N 21/2743* (2011.01)
*H04N 21/4223* (2011.01)

(56) References Cited

U.S. PATENT DOCUMENTS

| | | | | |
|---|---|---|---|---|
| 9,403,058 B2 * | 8/2016 | Tagliabue | | A63B 24/0062 |
| 9,457,228 B2 * | 10/2016 | Sinha | | H04N 5/772 |
| 9,566,471 B2 * | 2/2017 | DeAngelis | | A63B 24/0021 |
| 9,724,561 B2 * | 8/2017 | Sinha | | A63B 24/0003 |
| 2002/0115047 A1 * | 8/2002 | McNitt | | A63B 24/0003 |
| | | | | 434/252 |
| 2008/0200287 A1 * | 8/2008 | Marty | | A63B 24/0003 |
| | | | | 473/459 |
| 2010/0144414 A1 * | 6/2010 | Edis | | A63B 24/0006 |
| | | | | 463/8 |
| 2011/0304497 A1 * | 12/2011 | Molyneux | | A43B 1/0054 |
| | | | | 342/42 |
| 2012/0279311 A1 * | 11/2012 | Helmer | | A63B 24/0021 |
| | | | | 73/768 |
| 2012/0289354 A1 * | 11/2012 | Cottam | | A63B 69/3658 |
| | | | | 473/223 |
| 2013/0018493 A1 * | 1/2013 | Amini | | A63B 69/38 |
| | | | | 700/91 |
| 2013/0018494 A1 * | 1/2013 | Amini | | A63B 24/0006 |
| | | | | 700/91 |
| 2013/0178304 A1 * | 7/2013 | Chan | | A63B 69/36 |
| | | | | 473/266 |
| 2013/0184613 A1 * | 7/2013 | Homsi | | G01P 13/00 |
| | | | | 600/595 |
| 2013/0346009 A1 * | 12/2013 | Winter | | G01D 11/00 |
| | | | | 702/96 |
| 2014/0188426 A1 * | 7/2014 | Fastert | | G01P 15/0891 |
| | | | | 702/139 |
| 2014/0286621 A1 * | 9/2014 | Matsunaga | | G11B 27/10 |
| | | | | 386/241 |
| 2014/0372440 A1 * | 12/2014 | Cains | | A63B 71/145 |
| | | | | 707/737 |
| 2015/0016685 A1 * | 1/2015 | Matsunaga | | G09B 19/0038 |
| | | | | 382/103 |
| 2015/0029341 A1 * | 1/2015 | Sinha | | H04N 5/772 |
| | | | | 348/157 |
| 2015/0045153 A1 * | 2/2015 | Thurman | | A63B 69/38 |
| | | | | 473/553 |
| 2015/0109129 A1 * | 4/2015 | Merril | | G01P 15/0891 |
| | | | | 340/573.1 |
| 2015/0324636 A1 * | 11/2015 | Bentley | | G11B 27/17 |
| | | | | 386/227 |
| 2015/0352419 A1 * | 12/2015 | Pappas | | A63B 69/002 |
| | | | | 473/422 |
| 2016/0107063 A1 * | 4/2016 | Watanabe | | G06Q 10/0639 |
| | | | | 348/157 |
| 2016/0158626 A1 * | 6/2016 | Dolige | | G09B 19/0038 |
| | | | | 700/92 |
| 2016/0166912 A1 * | 6/2016 | Paredes | | A63B 69/38 |
| | | | | 473/462 |
| 2016/0184686 A1 * | 6/2016 | Sampathkumaran | | G09B 19/0038 |
| | | | | 434/247 |
| 2016/0328839 A1 * | 11/2016 | Aoki | | H04N 5/77 |

* cited by examiner

SPORT TRAINING EQUIPMENT

RELATED APPLICATIONS

This application is a continuation-in-part of U.S. patent application Ser. No. 15/268,538, filed Sep. 17, 2016, entitled "SPORT TRAINING EQUIPMENT", which is a continuation-in-part of U.S. patent application Ser. No. 14/326,470, filed Jul. 9, 2014, entitled "SPORT TRAINING EQUIPMENT", which claims priority to provisional application Ser. No. 61/843,919, entitled "SPORT TRAINING EQUIPMENT", filed Jul. 9, 2013, the specifications of which are hereby incorporated herein by reference.

FIELD OF THE INVENTION

The present invention relates generally to sport training, and more particularly, to system and method of capturing the video of swing motion in sports of hitting a ball by a player, for analysis and training.

BACKGROUND OF THE INVENTION

Participation in many sports involves repeating certain motions over and over again. The consistent ability to perform these motions in a particular way is usually critical to good performance in the sport. Different methods have been found to help participants develop the ability to repeatedly move in a certain way. Increasingly, technology is being used in such methods to improve performance in sports.

Video image analysis is an important part of modern sports training. The ability to see oneself perform a motion helps an individual identify flaws in technique and correct them. Furthermore, video image analysis techniques can be applied to video of a sports motion to help identify aspects of a motion that need changing or identify aspects of a motion performed correctly for positive feedback.

Taking tennis as an example, a tennis player's swing technique is critical to their ability to play different strokes like forehand topspin, backhand volley, serve, and variety of other strokes. Over the years, a preferred tennis swing technique for various strokes has been identified and most tennis players strive to model their swings as closely as possible to the preferred technique. Video image analysis has been used in tennis to improve tennis player's swings. Appropriate swing analysis can contribute to an improvement in the player's skill.

A straightforward form of video image analysis of a tennis sport for example, is simply to record a tennis player's swing for ground stroke, volley, or a serve, and watch it back to identify flaws that cannot be discerned by the player themselves or by a tutor. Video footage can be paused so that individual frames showing a particular swing position can be analyzed.

Another analysis method is to display a player's tennis swing next to that of another, to more easily identify differences compared to a model swing. Some existing methods involve synchronizing the two swings so that corresponding swing positions are shown together, which makes comparison easier.

When capturing video footage of a tennis swing for example, there may be a large amount of footage recorded either side of the swing itself, for example when a player is preparing to serve. Such footage is largely redundant and can make it difficult to quickly identify the actual swing motion and may take up precious memory space in the case of stored digital video data. It is therefore desirable to extract segments of video footage that contain just the swing motion for various strokes.

Some existing methods of golf swing video analysis achieve these aims, i.e. extraction of a segment of video containing a golf swing or identification key swing positions, or both.

Examples of such existing methods are: Manually examining the video swing footage and identifying the segment showing the tennis swing and frames showing key motion positions. This is time intensive as it requires a user to look through all the video footage.

Detecting the noise of impact to identify the moment of impact has been disclosed in U.S. Pat. No. 6,537,076 and U.S. Pat. No. 6,567,536. The rest of the swing is assumed to be within a certain time either side of this moment. This method requires an audio detection device working with the video capture device. This method will not reliably work when there is noise in the environment. For example, when other players are playing tennis in adjacent tennis courts, the sound of impact can be falsely detected due to another player's stroke.

Using other types of sensor to detect parts of the swing, for example pressure mats, are disclosed in U.S. Pat. No. 2006/0281060. However, this method may apply only for sport like golf and will not apply for sport like tennis, where the player needs to move from one position to other.

U.S. Pat. No. 8,020,098 B2 discloses an impact detection unit comprising of microphone which is placed near the player. This invention may work only in sports where the player is not moving around. This may not work all the time for all types of sport involving a player hitting a ball, for example tennis.

A variety of devices are known in the art that can measure parameters associated with a swing motion of a sport. These devices generally require that a player take swings at a ball while being monitored by launch monitors, video devices and other measuring devices. However, such devices suffer from several deficiencies. Foremost among these is cost. Some types of launch monitors generally use radar technology in conjunction with the Doppler effect to measure the speed and position of the swing and ball. These launch monitors must be capable of emitting the precise type of radar necessary, as well as analyzing the shift in frequency due to the Doppler effect, in order to provide useful information to the player. The launch monitors therefore tend to be expensive, and can be especially cost prohibitive for amateur players. In addition, launch monitors can require professional calibration and set up to be able to obtain accurate information.

One such system is disclosed in U.S. Pat. No. 7,736,242 B2. Such systems are integrated and embedded within the sport equipment. Hence these systems cannot be used for monitoring swing motion of any other sports.

Hence there is a need in the art for a system and method that would allow amateur and professional players alike to be able to capture and analyze various aspects of their swings in an accurate and cost effective manner. The training devices should be such that it can be reliably used for any sport involving an impact to the sport equipment. Players should be able to use already-owned and/or everyday-used portable electronic devices as a training device. There is also a need that a user should be able to use the same training device to monitor the swing motion of various sports like tennis, squash, golf, cricket, baseball, basketball and the like.

SUMMARY OF THE INVENTION

It is one object of the invention to provide an improved and cost effective device for analysis of a swing of a game device of a user.

Accordingly, a system is provided for recording, viewing and analyzing tennis swings or the like. The system starts out with a portable video image capture unit, preferably in the nature of a smartphone, having at least one digital camera for recording swings using one or more impact sensors. Upon activation, the digital recording means continuously records in a loop. A swing sensor, based on an impact trigger, directs the recording means to save a bracketed portion of the video, and to save it temporarily. The video image is then played back on a video screen portion of the unit, for the user to see. The user is then given the option of saving the swing for later viewing and analysis. Depending on the player's choice, the saved swing is then sent electronically to a remote site for further processing and storage. In addition, the viewing unit preferably has means for converting the video images, which may be saved by the capture unit in JPEG format, into MPEG format. The MPEG files are then automatically, or at the direction of the user, uploaded to the Internet via the viewing unit. The uploaded MPEG image files are then saved off-site. The user can then access the saved images at a remote PC or other web-enabled device. The image files are then viewable through a known media viewing application software.

According to one aspect of the invention there is provided an apparatus for use in detecting and analyzing a swing of a game, the device comprising:
a first component being an impact detection device, shaped and arranged to be attached to the sport equipment, the component including:
one or more impact sensing sensors;
a power supply;
a communication system for wireless communication with an exterior device;
and a second component being a portable camera device, including:
a camera supporting video recording or capturing of snapshots;
a compatible wireless communication system to send and receive signals to/from the impact detection device;
and an application program running on the portable camera device to receive information relating to the signals from the impact detection device and to process the signal to capture video recording of only the swing motion.

The impact detection device can be attached to the sport equipment, preferably the sport equipment is a tennis racket. However the same arrangement can be applied to other game devices such as golf clubs, baseball bats, cricket bats and other such devices intended to impact a game element such as a ball. The impact detection device can also be attached to other sport equipment like surfboard, skateboard, archery target board, basketball backboard, basketball net or the like. The impact detection device can be inserted as a sliding fit into the open end of a shaft of the game device or it can be attached to any other location which allows it to move with the device. The impact sensing device may include a housing which is easily removable from the game device and is transportable. The impact detection device can also be worn in the wrist while playing volleyball or can be attached to the leg/shoe while playing soccer for example.

The impact sensing device of one aspect is a stand-alone unit, and thus includes a housing. The housing is rugged to survive rigorous sporting activity. Preferably, the housing provides a universal interface which permits mounting of the unit to a variety of sports equipment, for example, onto a tennis racket, cricket bat, golf club, player's wrist, and the like. The universal interface is preferably a conformal surface which conveniently permits mounting of the sensing unit to a plurality of surfaces, e.g., a flat surface such as a cricket bat, and a round bar such as on a tennis racket handle or baseball bat.

According to another aspect of the invention there is provided an apparatus for use in detecting and analyzing a swing of a game, the device comprising:
a first component being an impact detection device, shaped and arranged to be attached to the sport equipment, the component including:
one or more impact sensing sensors;
a power supply;
a communication system for wireless communication with an exterior device;
and a second component being a portable camera device, including:
one or more impact sensing sensors;
a camera supporting video recording or capturing of snapshots;
a compatible wireless communication system to send and receive signals to/from the impact detection device;
and an application program running on the portable camera device to receive information relating to the signals from the impact sensors in impact detection device and portable camera device, and to process the signal to capture video recording of only the swing motion.

According to another aspect of the invention there is provided an apparatus for use in detecting and analyzing a swing of a game, the device comprising a portable camera device, including:
one or more impact sensing sensors;
a camera supporting video recording or capturing of snapshots;
and an application program running on the portable camera device to receive information relating to the signals from the impact sensing sensors and to process the signal to capture video recording of only the swing motion.

Preferably there is provided an arrangement for detecting the timing of an impact and wherein the application program is arranged to record the video image within a window on each side of the sensing of an impact.

Preferably the impact sensing sensor is a motion sensor to sense change in orientation, position, velocity, angular velocity, acceleration, angular acceleration, or the like due to impact.

Preferably the impact sensing sensor is a piezoelectric sensor to sense change in pressure, acceleration, force, or the like due to impact.

Preferably the impact sensing sensor is a sound sensor or microphone to sense air pressure variations of a sound wave generated due to impact.

Preferably the wireless communication is effected by Bluetooth.

Preferably the portable camera device includes a touch screen.

Preferably the impact sensing device includes a housing which is easily removable from the game device and is transportable.

Preferably the housing includes a slot portion which engages around the game device.

Preferably the Software is split into two parts: firmware that runs on the impact detection device and a software application running on the portable camera device.

Preferably the application program running on the portable camera device is arranged to provide an input of the type of sport and recording window time.

Preferably the firmware running on the impact detection device is responsible for detecting the impact, and transferring the impact detection signal wirelessly to the portable camera device and the software running on portable camera device is responsible for start/stop video recording, capture video for swing motion, save it in local memory, display of the captured swing motion, uploading the time stamped video to the internet.

Preferably the firmware running on the impact detection device can be in low power mode whenever possible to save battery life.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION OF THE INVENTION

Figure 1:
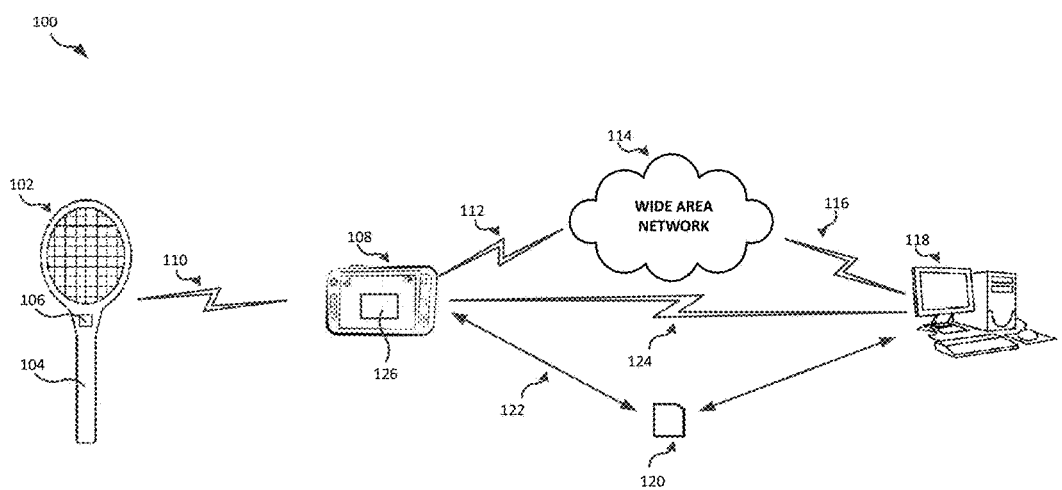
FIG. 1 is a schematic view of an example embodiment of sport swing video image recording system.

FIG. 1 is a schematic view of an example embodiment of sport swing video image recording system 100. System 100 includes impact detection device 106 and portable camera device 108. Impact detection device 106 and the portable camera device 108 communicate using a short range, low power wireless communication protocol link 110, and form part of a wireless personal area network (WPAN).

In operation of sport swing image video recording system 100, according to one embodiment of the invention, impact detection device 106 can be attached to an outside surface of racket system 102, or placed in an internal cavity. According to an embodiment of the invention, the impact sensing device 106 can be attached to the racket system 102 using a strap, VELCRO, tape, adhesive or other means.

According to another embodiment of the invention, the same impact sensing device 106, may be attached to any other sport equipment like cricket bat, baseball bat, squash racket, badminton racket, basketball net or the like, using straps, VELCRO, tape, adhesives or other means. According to another embodiment of the invention, the same impact sensing device 106, may also be attached to a player, for example using straps, VELCRO, tape, adhesives or other means to the player's wrist, arm or hip to detect impact with a ball in sports like volley ball, soft ball, soccer. Hence, a user playing different sports, can reuse the disclosed video image recording system for plurality of sports. The user will not need to buy separate monitoring system for individual sports, making the disclosed invention very cost effective. According to another embodiment of the invention, impact sensing device 106, may be placed near the vicinity of the player or play area.

The impact sensing device 106, according to preferred embodiment of the invention, generates a trigger event which may be caused by impact between the sport equipment and the ball or the like. In accordance with one embodiment, the trigger event is sensed by one or more impact sensors in impact sensing device 106 sensing impact to the sport equipment. The trigger event is then transmitted to the portable camera device 108 over wireless link 110. The portable camera device 108 uses the trigger event to capture a window of video image around the impact, thus capturing the swing or stroke motion. According to another embodiment of the invention, the trigger event is sensed by one or more impact sensors in portable camera device 108. According to another embodiment of the invention, the trigger event is sensed by one or more impact sensors in impact sensing device 106 and one or more impact sensors in portable camera device 108.

According to one aspect of the invention, the portable camera 108, upon capture of video image of sport motion involving impact with the sport equipment, can save the video in computer readable display format like JPEG or MPEG or the like.

According to one embodiment of the invention, portable camera 108 can comprise further interfaces, e.g. a GSM/3G or WiFi interface 112 to be connected with a central server in wide area network 114 being represented to be reached in the cloud/internet to conduct an offline analysis on the computer 118. The video images uploaded to internet, can be downloaded by computer 118 using a GSM/3G or WiFi or Ethernet interface 116. Such an offline analysis can also be achieved after transmittal of captured video data of the sports motion stored in the portable camera device 108, e.g. on a storage card 120 as an SD-card, which can be reached via a storage interface 122. The storage card 120 can be read in a computer 118 to conduct said analysis.

One embodiment of the invention is presentation of the video through an Internet connection 112 such that a player may participate in a remote lesson. As such, the portable camera 108 might communicate to the remote station 118 through an Ethernet, a wireless, or a TCP/IP protocol connection 112 and 116. In yet other embodiments, the portable camera 108 can download captured video to a hard disk, a floppy disc, a tape disk, a CD, or any other recordable medium allowing the player or instructor to download analysis information for later use.

According to one embodiment of the invention, a sports application 126 will run on the portable camera device 108. The role of this application will be to establish a wireless link with impact sensing device 106, to send commands and configuration parameters to 106, to receive impact detection notifications from 106, to record video image of the sports motion, to upload video image to internet and the like. In another embodiment of the invention, the sports application 126 will receive impact detection notifications from one or more impact sensors in portable camera device 108 to record video image of the sports motion. According to another embodiment of the invention, the sports application 126 will receive impact detection notifications from one or more impact sensors in portable camera device 108 and one or more impact sensors in impact sensing device 106 over established wireless link, to record video image of the sports motion.

Figure 16:
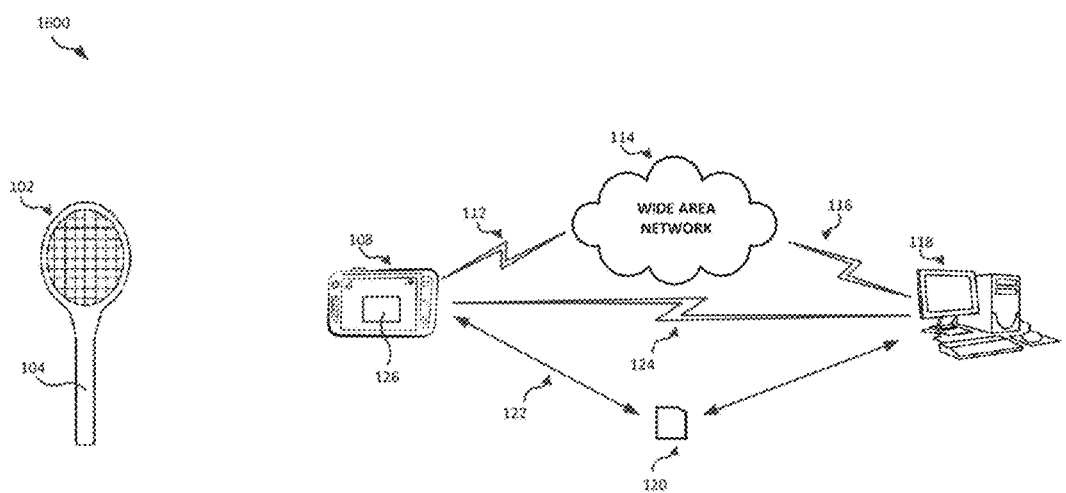
FIG. 16 is a schematic view of another example embodiment of sport swing video image recording system.

FIG. 16 is a schematic view of another example embodiment of sport swing video image recording system 1600. System 1600 includes portable camera device 108. The trigger event is sensed by one or more impact sensors in portable camera device 108. The sports application 126 will receive impact detection notifications from one or more impact sensors in portable camera device 108. The sports application 126 uses the trigger event to capture a window of video image around the impact, thus capturing the swing or stroke motion.

Figure 2:
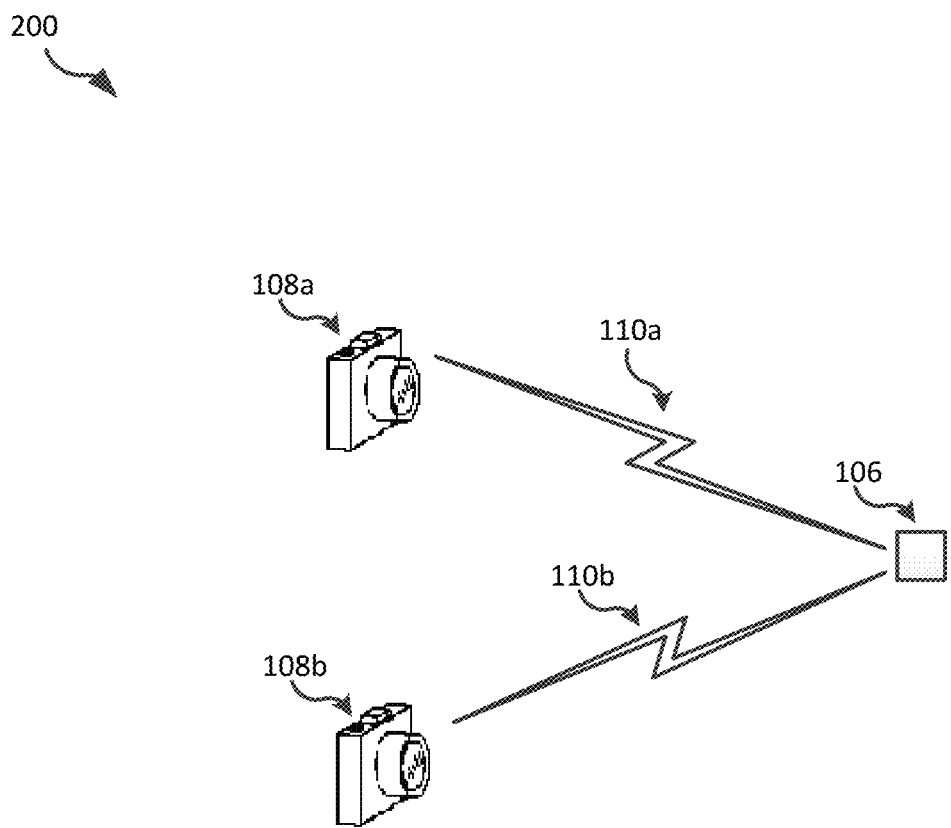
FIG. 2 illustrates a schematic diagram of an example embodiment of sport swing video image recording system where multiple portable camera devices are used to capture the sport motion using one impact detection device.

According to one embodiment of the invention, more than one portable camera device 108 may be used simultaneously to capture, from different viewing angles, the sport motion involving an impact of the sport equipment with a sport ball or the like. This may be done to view the same stroke from different angles and to better assist the player in improving the sport performance. FIG. 2 illustrates a schematic diagram of such an example embodiment where two portable camera devices 108a and 108b are used to capture the sport motion using one impact detection device 106. In such an embodiment, the impact detection device 106 may transmit the impact notification data to both the portable camera device 108a and 108b, to which it is wirelessly connected by the link 110. According to one aspect of the invention, the impact detection device 106 may multi-cast the impact notification to each of the wirelessly connected portable camera device 108, at the same time. According to another aspect of the invention, the impact detection device 106, may unicast the impact notification individually to each of the plurality of wirelessly connected portable camera device 108. According to another aspect of the invention, the plurality of portable camera devices 108a and 108b may use impact notification from impact sensors present in the corresponding portable camera device.

Figure 3:
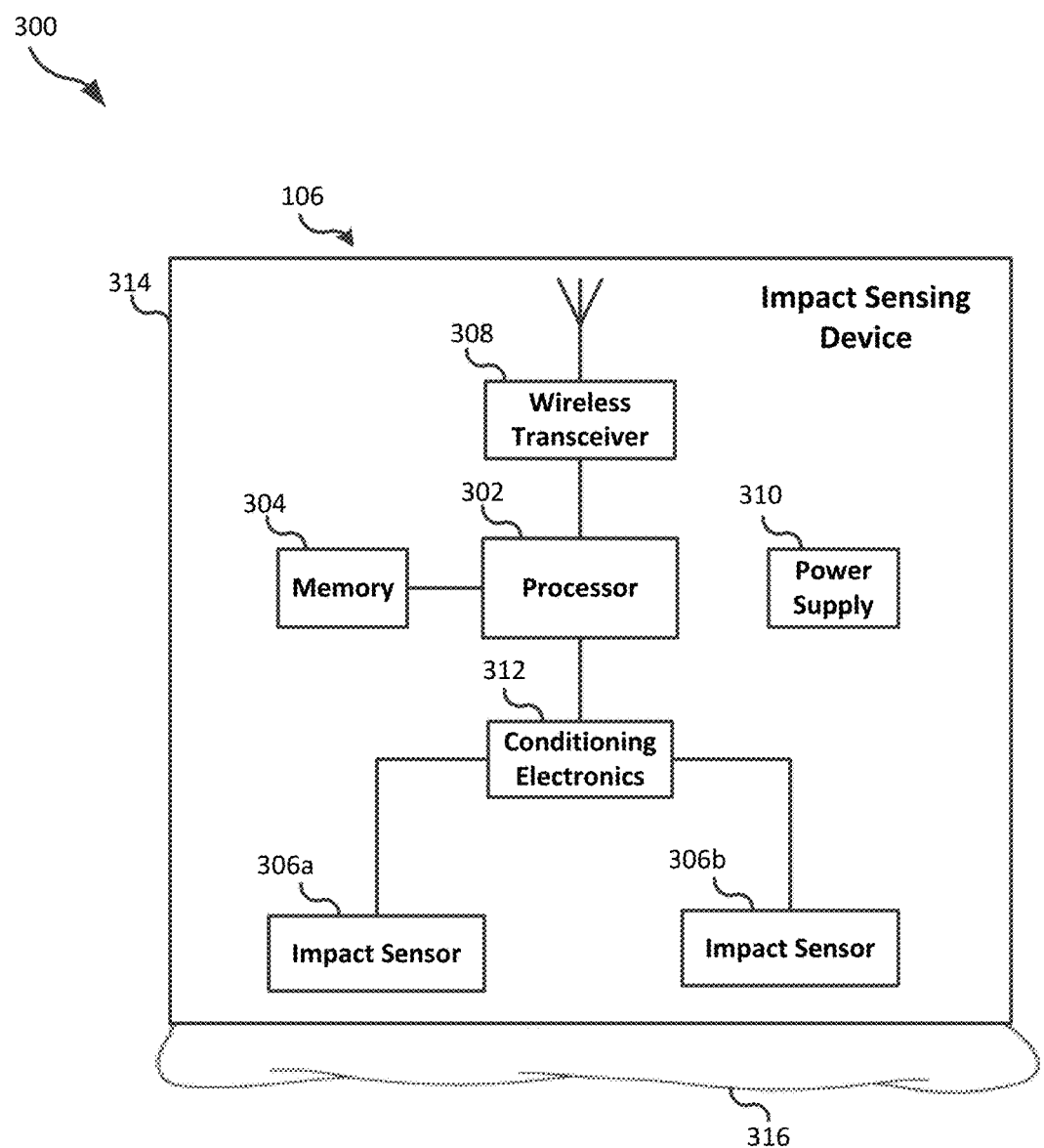
FIG. 3 illustrates a schematic diagram showing components provided in one example of an impact detection device according to an embodiment of this invention.

FIG. 3 illustrates a schematic diagram showing components provided in one example of an impact detection device 106 according to an embodiment of this invention. As illustrated, impact detection device 106 includes a processor 302, impact sensors 306a and 306b, power supply unit 310, memory 304, and a short-range, low power wireless transceiver 308.

Processor 302 is a conventional processor such as, for example, a microcontroller capable of implementing application programs stored in memory 304. Processor 302 is coupled to memory 304, impact sensors 306a and 306b, and short-range, low power wireless transceiver 308. In some embodiments, impact sensor 306 may connect to the processor 302 through a conditioning electronics unit 312.

Memory 304 is used to store firmware program instructions and data. In an embodiment, memory 304 stores programs, for example, used to make a wireless connection with the portable camera device 108, to detect impact and send impact notification to portable camera device 108. In an embodiment, memory 304 includes both read only memory and random access memory. In addition, memory 304 may store timestamps of impact.

Impact sensors 306a and 306b detect when an impact is made between the sport equipment, to which the impact sensing device 108 is attached to, and a ball or the like. In an embodiment of the invention, impact sensors 306a and 306b may also provide information related to extent of impact. One or more impact sensors may be present in the impact detection device 106. In an example embodiment of the invention, plurality of impact sensors is selected from the group comprising of piezo-electric sensor, sound sensor, motion sensor. The motion sensors may for example include an accelerometer, a rate gyroscope, magnetometer, infrared sensor, image sensor, and potentially other sensors to detect motion, position or orientation.

In a preferred embodiment of the invention, plurality of impact sensors 306a and 306b is mounted on a rigid surface. In a further embodiment of the present invention, the plurality of impact sensors can be mounted on a target pad where each of the plurality of impact sensors provide an analog output indicative of the characteristic of an object impacting the target pad. When the impact sensor like piezo-electric sensor, motion sensor, microphone senses impact to the sport equipment, the sensor produces an electrical voltage signal, which can be detected and utilized to provide a tangible indication of the occurrence and/or the force of the impact.

In one embodiment of the invention, the impact sensor 306a and 306b is operatively connected by wiring to an amplifier as part of conditioning electronics unit 312. The amplifier can increase the signal produced by the impact sensors 306a and 306b to ensure the signal is distinguishable from any electrical noise that may be present. After amplification, the signal can be transmitted to an analog to digital converter, also part of the electronics conditioning unit 312, and sent to a processor 302. The processor 302, upon detecting the impact signal, may send an impact notification to the portable camera device 108 over the established wireless link.

According to another embodiment of the invention, the processor 302 may convert the input signal to a force value. The electric signal produced by the plurality of impact sensors 306a and 306b, of the preferred embodiment, will have an amplitude that is a function of the force of the blow. The value of this amplitude is received by the processor 302, which converts the amplitude to a force value. This force value may then be preferably sent to a remote portable camera device 108.

In one embodiment of the invention, the voltage signals generated from the impact sensor can be passed to a front end amplifier, as part of the conditioning electronics 312, which can comprise a MOSFET or JFET amplifier in a voltage follower configuration. The input impedance of this voltage follower can be adjusted so that a signal of the proper voltage level is coupled to the next stage. Its offset voltage is also adjustable to obtain preferably a zero offset voltage. The front end amplifier can be designed to match the transducer signals and circuitry to the downstream detector circuitry, and can be readily selected from well known circuitry. This matching capability is desirable because the output from the impact sensor can vary with different sport.

In another embodiment of the invention, the voltage signal generated from the impact sensor can be passed to a front end amplifier and then to the next stage which is a peak detector, as part of the conditioning electronics 212. The peak detector is basically a rectifying circuit that detects the peak voltage of the incoming signal in response to the strength of the blow delivered to the sport equipment. The voltage output of the peak detector is able to hold in known fashion for a short time to allow the processor 202 to capture the peak value, indicative of the velocity of the blow applied. The holding time can be adjusted by the time constant of a capacitor and resistor network in the peak detector at the output end.

In another embodiment of the invention, the output of the impact sensor is directed to a voltage comparator, as part of the conditioning electronics 312. The output of the voltage comparator is a function of the difference between the voltage generated by the impact sensor and another predetermined threshold value. Only signals exceeding the threshold values are passed on, the other being discarded. The signal from the comparator can be sensed by the processor 302 as a function of the magnitude of the force of an impact. In another embodiment of the invention, various signal processing filters known in the art are applied to the electrical signal output from the impact sensors, as part of the conditioning electronics 312. In another embodiment of the invention, various signal processing filters known in the art are applied by processor 302 to the electrical signal output from the impact sensors, to detect impact. In one example embodiment, Gaussian filter may be applied. In another example embodiment, low-pass filter may be applied. In another example embodiment, high-pass filter may be applied. In another example embodiment, band-pass filter may be applied.

Wireless transceiver 308 is a short range, low-power transceiver used to communicate with the portable camera device 108. In a preferred embodiment, transceiver 308 operates in an unlicensed frequency band such as 2.4 GHz using Bluetooth Low Energy (BLE) wireless communication protocol. As used herein, the term transceiver means a combination of a transmitter and a receiver. In an embodiment, the transmitter and the receiver are integrated and form, for example, a part of an integrated circuit. In other embodiment, transceiver 308 can be a WiFi, Zigbee, ANT or other short range, low power wireless transceiver.

Power supply unit 310 is used to provide power to operate the various components of impact sensing device 106. In an embodiment, power supply unit 310 can either be a rechargeable battery or a non-rechargeable battery that must be periodically replaced or a solar cell. A battery, preferably secured to the piece of athletic equipment in a non-contact area, is used to provide the power necessary to amplify, process, store and/or transmit the information received from the impact. The power supply unit 310, in one embodiment of this invention, can have a switch, not shown in FIG. 2, for the user to turn on and off the power supply to the components of the impact sensing device 106. When the impact needs to be monitored by the portable camera device 108, for video image capture, the power supply switch can be turned on and when the impact monitoring is done, the power supply switch can be turned off to save power.

In another embodiment of the invention, the impact sensing device 106 can include low power mode of operation, and may not have any switch for controlling the power supply. The impact sensing device 106 can always have power supply from the power supply unit 310, and it can enter low power mode by de-activating the wireless transceiver 308 when no impact is detected. The impact sensing device 106 may wakeup and activate the wireless transceiver 308 only when an impact is detected. After transmitting the impact notification to portable camera device 108, the impact sensing device 106 can go back to low power mode.

In preferred embodiment of this invention, the impact sensing device 106 can be a standalone dedicated device with an attachment device. The attachment device can be used to clip the apparatus to a racket, to golf club, to a cricket bat, to a baseball bat, to a wrist band, or the like. It should also be understood that any suitable attachment device may be incorporated into the apparatus. For instance, in other embodiments, the attachment device may comprise an adhesive, a strap such as a wristband, or the like.

In yet another embodiment of this invention, the impact sensing device 106 can consist of a custom made printed circuit board and a plastic enclosure using a TI CC2540 2.4 GHz Bluetooth Low Energy System-on-Chip Solution with 256 KBytes program flash and 8 KBytes of RAM, which is connected to plurality of impact sensors comprising of a motion sensor, 3-axis accelerometer LIS2DH, by STMicroelectronics, piezoelectric sensor from Murata, and microphone from InvenSense. This System-on-chip solution has a processor 302, memory 304, Bluetooth Low Energy (BLE) transceiver 308 integrated. The impact sensing unit can be supplied with power by a 3.7 Volt lithium-polymer rechargeable battery (310).

In yet another embodiment of this invention, the impact sensing device 106 can comprise of a double-sided printed circuit board. The Bluetooth Low Energy (BLE) transceiver 308 and the plurality of impact sensors can be mounted on one side, e.g. the top layer, while the microcontroller 302 and the analog circuits can be provided on the other side, e.g. on the bottom layer.

In one embodiment of this invention, in order to provide for prolonged battery lifetime of the impact sensing device 106 can be adapted for low-power operation. The analog sensor circuit 306 and the processor 302 can be put into low-power mode most of the time to reduce the overall power consumption. As a result, the biggest part of the power budget is assigned to the Bluetooth Low Energy (BLE) module 308. By duty-cycling the Bluetooth Low Energy (BLE) module 308 when connected, the total current drawn of the impact sensing device 106 can be reduced significantly. To prevent a sudden power failure, the battery voltage can be measured continuously and displayed on the portable camera device 108.

According to one embodiment of the invention, the impact sensing device 106 is generally enclosed by an appropriate housing 314, such as a plastic injected molded housing known in the art. The housing 314 is rugged to withstand the elements such as snow, water and dirt. The housing 314 cooperate so as to provide an environmentally secure enclosure for the electronics such as the microprocessor 302 while providing an operable interface to communicate with the system. The housing 314 preferably includes a universal interface 316 which provides flexible and conformal mounting to a variety of surfaces, such as to the relatively flat surface of a cricket bat or to a round bar on a tennis racket. The universal interface 316 is designed to permit stand alone units 106 to be sold in stores regardless of how or where a user mounts the unit, to sense impact during sport motion.

In an embodiment, the housing 314 of the impact detection device 106 may be releasably attached to universal interface 316. In an alternative embodiment, the housing 314 may be permanently fixed to or integrally formed with the universal interface 316.

Figure 4A:
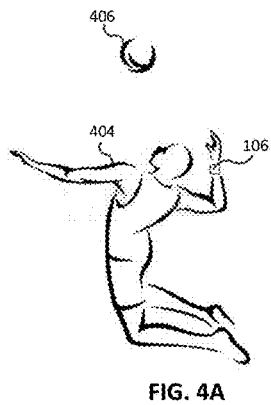
FIG. 4A-4I shows various example sports where the same impact detection device can be attached to record video image of the sport swing or stroke for sport training purposes.
Figure 4B:
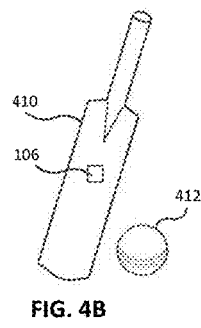
Figure 4C:
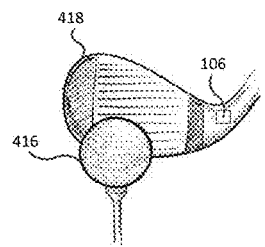
Figure 4D:
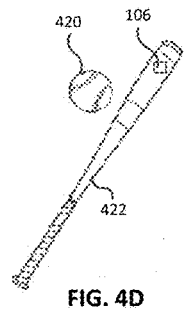
Figure 4E:
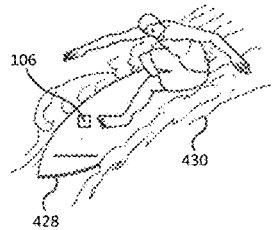
Figure 4F:
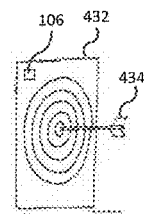
Figure 4G:
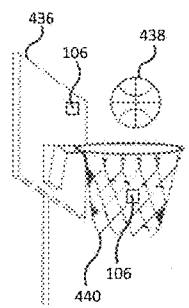
Figure 4H:
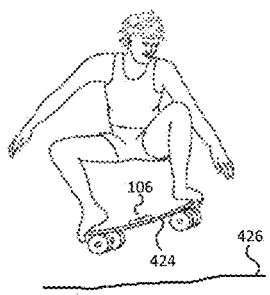
Figure 4I:
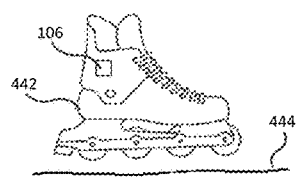

FIG. 4A-4I shows various example sports where the same impact detection device 106 can be attached to record video image of the sport swing or stroke for sport training purposes. FIG. 4A-4I shows impact detection device 106 being attached to various sport equipment or worn by player to detect sport activity impact. FIG. 4A shows an impact detection device 106 being worn in the wrist of a volley ball player 404 to detect the impact when the player hit the volley ball 406. FIG. 4B shows an impact detection device 106 being attached to a cricket bat 410 to detect the impact when the bat hit the cricket ball 412. FIG. 4C shows an impact detection device 106 being attached to a golf club 418 to detect the impact when the club hit the golf ball 416. FIG. 4D shows an impact detection device 106 being attached to a baseball bat 422 to detect the impact when the bat hit the baseball 420. FIG. 4E shows an impact detection device 106 being attached to a surfboard 428 to detect the impact when the surfboard hit the water 430. FIG. 4F shows an impact detection device 106 being attached to an archery target board 432 to detect the impact when the arrow 434 hit the target board. FIG. 4G shows an impact detection device 106 being attached to a basketball backboard 436 to detect the impact when the basketball 438 hit the backboard. FIG. 4G also shows an impact detection device 106 being attached to a basketball net 440 to detect the impact when the basketball 438 hit the net. FIG. 4H shows an impact detection device 106 being attached to a skateboard 424 to detect the impact when the skateboard hit the ground 426. FIG. 4I shows an impact detection device 106 being attached to a roller blade 442 to detect the impact when the roller blade hit the ground 444.

Figure 5:
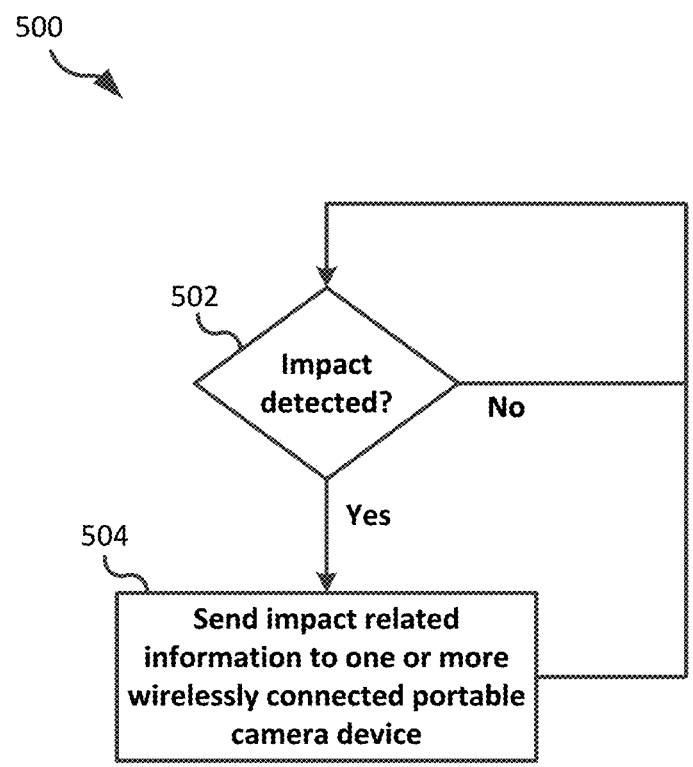
FIG. 5 illustrates an example flow chart of a process that may be performed by an impact detection device in accordance with an embodiment of this invention.

FIG. 5 shows an example flowchart detailing a process 500 for an impact detection device 106 to notify to the portable camera device 108, the occurrence of an impact between the sports equipment with which it is attached and a ball or the like, in accordance with an embodiment of the invention. The process 500 will be executed only after a wireless connection is established between the impact detection device 106 and the one or more portable camera device 108. Process 500 begins at step 502 when a determination is made if an impact is detected. If it is determined that an impact has occurred, then the processing proceeds to step 504, otherwise, the processing goes back to step 502. At step 504, the impact detection device 106 will send the impact related information to the one or more wirelessly connected portable camera device 108 over the established wireless link. In another embodiment of the invention, the impact detection device 106 will send the impact related information to the one or more portable camera device 108 over the wired connection. The impact information, according to an embodiment of the invention, can consist of a notification message regarding occurrence of the impact and may also contain impact force related information.

Figure 6:
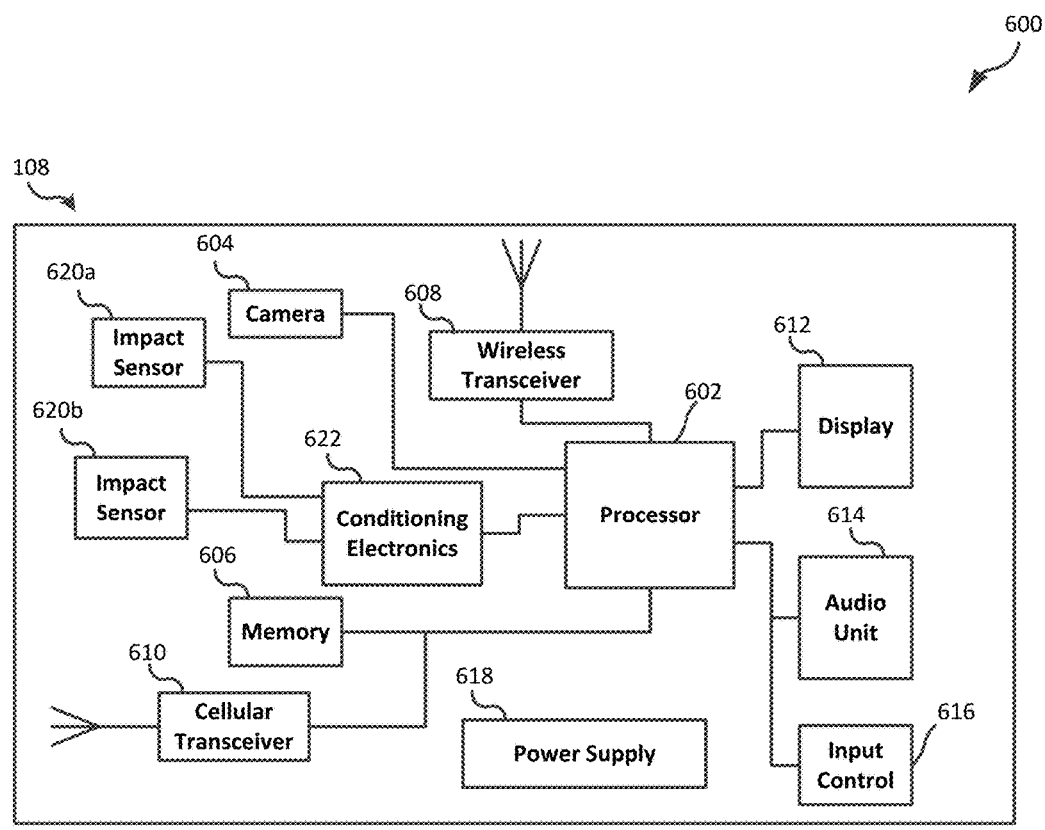
FIG. 6 illustrates a schematic diagram showing components provided in one example of a portable camera device according to an embodiment of this invention.

FIG. 6 is a schematic diagram 600 of an example portable camera device 108 according to an embodiment of the present invention. In an embodiment, portable camera device 108 may include, but is not limited to: a smartphone, a mobile phone, PDA device, a desktop computer, portable computer, tablet computer, a processor disposed in a digital camera, and/or any other device including a processor having at least one camera and a sport motion capture operation mode. As shown in FIG. 6, portable camera device 108 includes a processor 602, general purpose video camera 604, memory 606, a user input control 616, a display 612, an audio unit 614, a short-range, low power wireless communication transceiver 608, a cellular transceiver 610, a power supply unit 618, plurality of impact sensors 620*a* and 620*b*.

According to one embodiment, processor 602 is a conventional processor capable of implementing application programs stored in memory 606. Processor 602 is also capable of implementing digital signal processing algorithms and filters known in the art. Processor 602 is coupled to digital camera 604, memory 606, user input control 606, display 608, audio unit 610, wireless communication transceiver 608 and cellular transceiver 610. In another embodiment, processor 602 is also coupled to plurality of impact sensors 620*a* and 620*b*.

Impact sensors 620*a* and 620*b* detect when an impact is made between the sport equipment and a ball or the like. In an embodiment of the invention, impact sensors 620*a* and 620*b* may also provide information related to extent of impact. One or more impact sensors may be present in the portable camera device 108. In an example embodiment of the invention, plurality of impact sensors is selected from the group comprising of piezo-electric sensor, sound sensor, image sensor. In a further embodiment of the present invention, each of the plurality of impact sensors provide an analog output indicative of the characteristic of an impact with sport equipment. In one embodiment of the invention, the impact sensor 620*a* is a microphone, which senses sound due to impact to the sport equipment, the sensor produces an electrical voltage signal, which can be detected and utilized to provide a tangible indication of the occurrence and/or the force of the impact. In another embodiment of the invention, the impact sensor 620*b* is an image sensor, which senses optical image motion due to impact to the sport equipment. The image sensor 620*b* produces electrical signals as image signals, which can be detected and utilized to provide a tangible indication of the occurrence and/or the force of the impact. In one embodiment of the invention, the image sensor is made up of a photoelectric conversion element and an analog front end (AFE). The photoelectric conversion element may be, for example, a complementary metal oxide semiconductor (CMOS) type photoelectric conversion element. The photoelectric conversion element receives an image of a subject incident from the optical lens. The photoelectric conversion element photoelectrically converts the image of the subject and accumulates image signals for a predetermined time, and sequentially supplies the accumulated image signals, as analog signals, to the AFE. The AFE carries out a variety of signal processing, such as analog-to-digital (A/D) conversion, on the analog image signals. Through the signal processing, digital signals are generated, which are outputted as output signals.

In one embodiment of the invention, the impact sensor 620a and 620b is operatively connected by wiring to an amplifier as part of conditioning electronics unit 622. The amplifier can increase the signal produced by the impact sensors 620a and 620b to ensure the signal is distinguishable from any electrical noise that may be present. After amplification, the signal can be transmitted to an analog to digital converter, also part of the electronics conditioning unit 622, and sent to a processor 602.

According to another embodiment of the invention, the processor 602 may convert the input signal to a force value. The electric signal produced by the plurality of impact sensors 620a and 620b, of the preferred embodiment, will have an amplitude that is a function of the force of the blow. The value of this amplitude is received by the processor 602, which converts the amplitude to a force value.

In one embodiment of the invention, the voltage signals generated from the impact sensor can be passed to a front end amplifier, as part of the conditioning electronics 622, which can comprise a MOSFET or JFET amplifier in a voltage follower configuration. The input impedance of this voltage follower can be adjusted so that a signal of the proper voltage level is coupled to the next stage. Its offset voltage is also adjustable to obtain preferably a zero offset voltage. The front end amplifier can be designed to match the transducer signals and circuitry to the downstream detector circuitry, and can be readily selected from well known circuitry. This matching capability is desirable because the output from the impact sensor can vary with different sport.

In another embodiment of the invention, the voltage signal generated from the impact sensor can be passed to a front end amplifier and then to the next stage which is a peak detector, as part of the conditioning electronics 622. The peak detector is basically a rectifying circuit that detects the peak voltage of the incoming signal in response to the strength of the blow delivered to the sport equipment. The voltage output of the peak detector is able to hold in known fashion for a short time to allow the processor 602 to capture the peak value, indicative of the velocity of the blow applied. The holding time can be adjusted by the time constant of a capacitor and resistor network in the peak detector at the output end.

In another embodiment of the invention, the output of the impact sensor is directed to a voltage comparator, as part of the conditioning electronics 622. The output of the voltage comparator is a function of the difference between the voltage generated by the impact sensor and another predetermined threshold value. Only signals exceeding the threshold values are passed on, the other being discarded. The signal from the comparator can be sensed by the processor 602 as a function of the magnitude of the force of an impact. In another embodiment of the invention, various signal processing filters known in the art are applied to the electrical signal output from the impact sensors, as part of the conditioning electronics 622. In another embodiment of the invention, various signal processing filters known in the art are applied by processor 602 to the electrical signal output from the impact sensors, to detect impact. In one example embodiment, Gaussian filter may be applied. In another example embodiment, low-pass filter may be applied. In another example embodiment, high-pass filter may be applied. In another example embodiment, band-pass filter may be applied.

According to one embodiment, camera 604 may be a high-speed camera capable of recording audio and/or visual information. In some cases, the high-speed camera may record video images. In other cases, the high-speed camera may record multiple still images taken at a rapid rate. In one embodiment, the high-speed camera may capture information at a rate from 600 to 1200 frames per second. In some cases, the camera may capture information at a rate from 30 to 600 frames per second. In another embodiment, camera 604 may be either a high or a low resolution camera.

In still other cases, camera 604 may be configured to capture three-dimensional images and/or video. For example, in some embodiments a 3D camera including multiple lenses may be configured to capture three-dimensional images and/or video. In another embodiment, multiple cameras may be disposed at different locations to capture different views of an object used to create composite three-dimensional images and/or video.

Memory 606 is used to store application program instructions and data. In an embodiment, memory 606 stores programs, for example, used to implement all of the functionality of a typical smartphone, mobile phone, PDA or any other portable camera device and one or more programs used to implement aspects of the functionality of sport motion recording system 100 described herein. In an embodiment, memory 606 includes both read only memory and random access memory.

In another embodiment, the memory 606 can be a volatile memory such as DRAM. In this embodiment, DRAM is used as the memory of the processor 602 and has 512M bytes (or more) in capacity. Generally, size of video data is relatively large and a hard disk device is used to store the video data transmitted from the camera 604. On the other hand, DRAM is quite higher than hard disk devices in access speed. In order to quickly write and read the video data, the processor 602 of this embodiment has the memory without a hard disk device.

In another embodiment of the invention, memory 606 may be any known type of storage medium, including known magnetic or optical storage media, and may further include removable and/or portable media. For example, in some embodiments, storage medium 606 may include a portable memory card or other storage medium that may have the player's captured image data stored upon it. The portable memory card or other storage medium may be given to the player or coach for later retrieval or use.

According to one embodiment of the invention, the portable camera device 108 will run a sports application 126 to capture video image of a sport swing motion. In accordance with aspects of the invention, typically the sports application will be a software application running on processor 602. In accordance with an embodiment, the sports application uses the in-house camera 604 to record a physical motion. The physical motion can be a swing, stroke, jump, throw, a catch or the like involving an impact with the sport equipment. The sports application 126 will receive video signals from the camera 604 and will also receive impact information signal from the impact sensing device 106, and will synchronize both these signals to capture a window of video image of the sport motion around the impact. In another embodiment of the invention, the sports application 126 will receive video signals from the camera 604 and will also receive impact information signal from the one or more impact sensors 620a and 620b, and will synchronize all these signals to capture a window of video image of the sport motion around the impact. The video image information is then used to provide physical motion correction and instruction.

User input control 616 is used by an individual to interact with portable camera device 108. In one embodiment of the invention, user input control 616 can be used to control the sport application 126. In an embodiment, user input control 616 includes a variety of input buttons and/or keys. The function of each of these buttons and/or keys is typically determined based on an operating mode of portable camera device 108. In one embodiment, user input control 616 includes a touch pad or scroll pad and/or touch screen buttons.

Display 612 is used to display video of the swing motion to a user. In an embodiment, display 612 is a liquid crystal display. In one embodiment, the display 612 is configured to allow a user to view and/or interact with image/video information obtained with system 100, including allowing a user to analyze captured information associated with the sport swing of a player. Display 612 may not be present in some embodiment of portable camera device 108.

Audio unit 614 is used to process audio signals. In an embodiment, audio unit 614 converts, for example, digital audio signals into amplified analog audio signals that can be used to drive one or more speakers. In an embodiment, audio unit 614 implements signal processing algorithms such as those available from Dolby Laboratories, Inc., which enhance the quality of music.

Wireless transceiver 608 is a short range, low-power transceiver used to communicate with impact sensing device 106. In a preferred embodiment, wireless transceiver 608 operates in an unlicensed frequency band such as 2.4 GHz using Bluetooth Low Energy (BLE) wireless communication protocol.

Power supply unit 618 is used to provide power to operate the various components of portable camera device 108. In an embodiment, power supply unit 618 can be a battery recharged periodically using a power adapter that plugs into a typical household power outlet. Power supply unit 618 can also be a non-rechargeable battery.

Cellular transceiver 610 is used to send and receive, for example, voice cellular telephone signals. Cellular transceiver 610 can also be used to exchange information with a computer network such as, for example, the Internet. As used herein, the term cellular transceiver means a combination of a cellular transmitter and a cellular receiver. In an embodiment, the transmitter and the receiver are integrated together into a single device.

In one embodiment, cellular transceiver 610 can be used to upload captured video data described herein to the internet, from where the same data can be downloaded to a remote computer and analyzed, for example, by a player or a coach. For example, the coach can watch the swing motion in real time. The portable camera device 108 can continuously upload the captured swing motion video data to the internet web server. The coach of the player can, at any time, remotely log-in from anywhere to the web server using a computer, and analyze the swing motion.

Referring to FIG. 1, the impact sensing device 106 and portable camera device 108 establish a two way wireless communication 110 between them so that applications running on both devices may convey a range of programming, status, command, impact related information and the like. The wireless connection will be established as per the wireless protocol for the wireless technology being used. In a preferred embodiment of the invention, Bluetooth Low Energy (BLE) wireless protocol can be used and the connection for two way communication will be established as per the Bluetooth Low Energy (BLE) standard. The impact sensing device 106 and the portable camera device 108 will use the same wireless communication protocol.

According to one preferred embodiment of the invention, the impact sensing device 106 will need to be initially authenticated, paired and bonded with the portable camera device 108. The portable camera device 108 can utilize Bluetooth Low Energy (BLE) wireless communication technology for enabling a pairing with the impact sensing device 106. Bluetooth Low Energy (BLE) wireless technology allows a device to interpret respective Bluetooth Low Energy (BLE) profiles. The Bluetooth Low Energy (BLE) profiles specify applications and general operating behaviors so that Bluetooth Low Energy (BLE) enabled devices can autonomously communicate with other Bluetooth Low Energy (BLE) enabled devices and exchange information without a user initiating the communication. The Bluetooth Low Energy (BLE) profiles utilize settings to parameterize and control the communications between two Bluetooth Low Energy (BLE) enabled devices from the commencement of the communication. The Bluetooth Low Energy (BLE) profiles are efficient in saving time without having to repeatedly transmit parameters each time a previously established Bluetooth Low Energy (BLE) enabled device is re-engaged for communication. The linking of two devices is known as pairing. When initiating a link between two Bluetooth Low Energy (BLE) enabled devices for the first time, a user is instructed to follow a respective procedure which will establish a communication link between each device. During the procedure, the devices will exchange their Bluetooth addresses and possibly other information. Each Bluetooth Low Energy (BLE) device has a unique device address that is commonly referred to as the device Bluetooth Address. The Bluetooth addresses, and possibly other information, are stored so that when the two Bluetooth Low Energy (BLE) devices initiate communication thereafter, the respective Bluetooth Low Energy (BLE) devices will automatically establish a communication link without having to pair again. As a result, one of the devices will transmit advertisement events, which are basically broadcast inquiries for determining if any device in the vicinity is an already paired device that desires to utilize its services; however, a response to the communication will only be autonomously performed if the two enabled Bluetooth Low Energy (BLE) devices have previously been paired.

Figure 7:
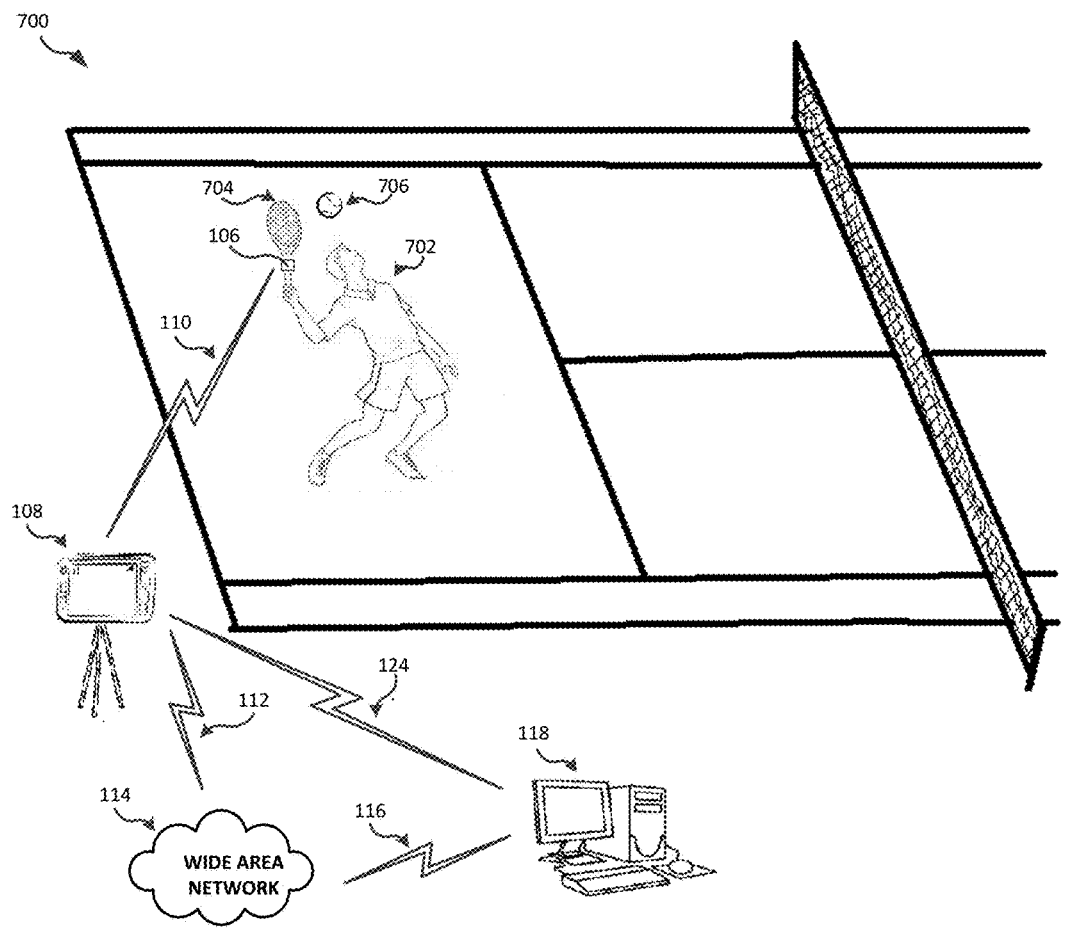
FIG. 7 is an isometric view of an exemplary embodiment of a system for obtaining video image capture of a tennis player's swing for analysis.

FIG. 7 is an isometric view of an exemplary embodiment of a system 700 for obtaining video image capture of a tennis player's swing for analysis. The impact detection device 106 is attached to the tennis racket 704. The portable camera 108 is placed in a position to capture video image from a viewing angle facing towards the side of the tennis player 702. The portable camera device 108 is placed in a capture mode by running the sport application. Whenever the tennis player 702 strikes the tennis ball 706, the impact detection device 106 will detect the impact and send an impact notification signal over the wireless link 110 to the portable camera device 108. Upon receiving the impact notification signal from impact detection device 106, the sport application running on portable camera device 108 will capture a window of video image of the strike and will save it in its permanent storage. The saved videos may be automatically uploaded by the sport application to the internet, for viewing and analysis later, using the interface 112 or can later be viewed in the portable camera device 108 itself. The saved videos can also be transferred directly to a remote computer 118 for viewing and analysis over wired or wireless link 124. The saved videos can also be downloaded by remote computer 118 from the internet over the wired or wireless interface 116. In another embodiment of the invention, the sport application running on portable camera device 108 will capture a window of video image of the strike based on impact notification from impact detection device 106, and one or more impact sensors located within the portable camera device 108.

Figure 17:
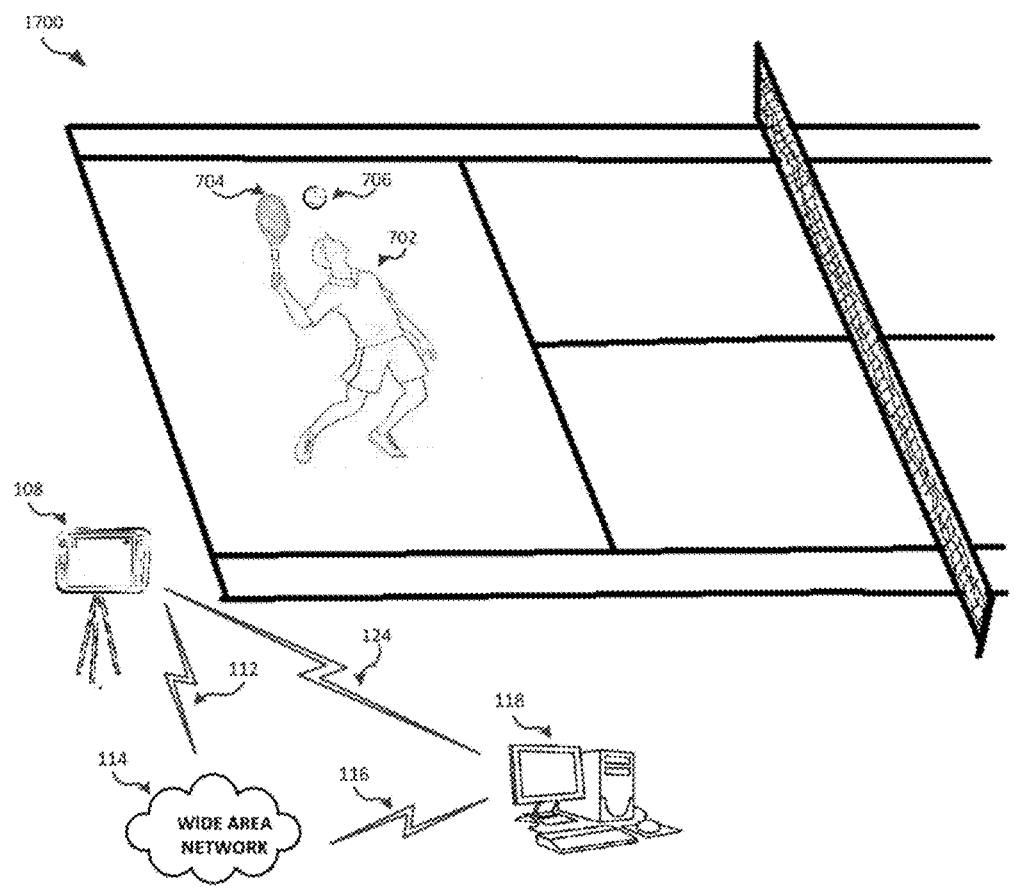
FIG. 17 is an isometric view of another exemplary embodiment of a system for obtaining video image capture of a tennis player's swing for analysis.

FIG. 17 is an isometric view of an exemplary embodiment of a system 1700 for obtaining video image capture of a tennis player's swing for analysis. The portable camera 108 is placed in a position to capture video image from a viewing angle facing towards the side of the tennis player 702. The portable camera device 108 is placed in a capture mode by running the sport application. Whenever the tennis player 702 strikes the tennis ball 706, the impact detection sensors in portable camera device 108 will detect the impact. Upon receiving the impact notification signal, the sport application 126 running on portable camera device 108 will capture a window of video image of the strike and will save it in its permanent storage. The saved videos may be automatically uploaded by the sport application to the internet, for viewing and analysis later, using the interface 112 or can later be viewed in the portable camera device 108 itself. The saved videos can also be transferred directly to a remote computer 118 for viewing and analysis over wired or wireless link 124. The saved videos can also be downloaded by remote computer 118 from the internet over the wired or wireless interface 116.

Figure 8:
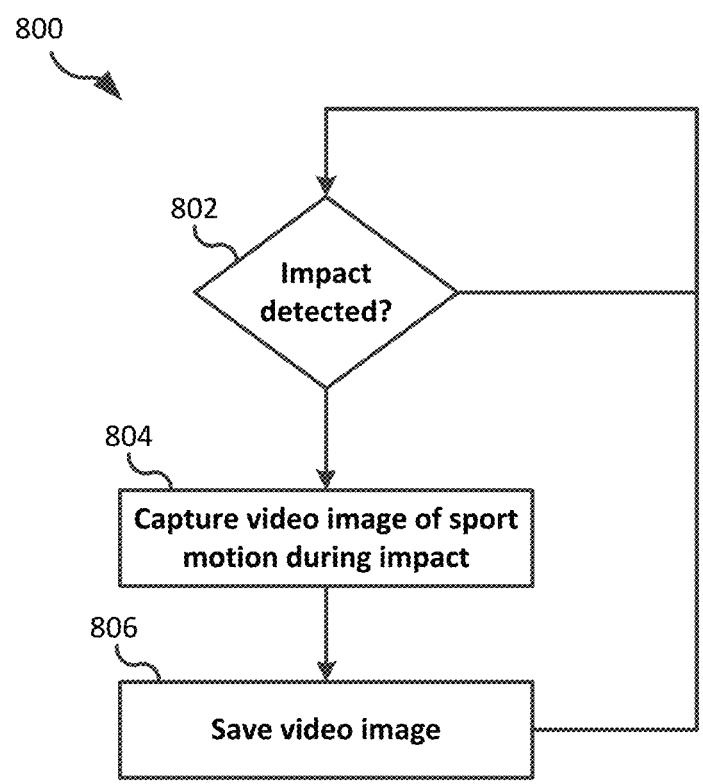
FIG. 8 illustrates an example flow chart of a process that may be performed by the portable camera device in accordance with an embodiment of this invention.

FIG. 8 shows an example flowchart detailing a process 800 for the portable camera device 108 to accomplish sports motion or swing video image capture of a sport player during impact between the sport equipment and the ball, in accordance with an embodiment of the invention. In one embodiment of the invention, the process 800 will be executed by the sport application running on the portable camera device 108 only after a wireless connection is established between the impact detection device 106 and the portable camera device 108. In another embodiment of the invention, where impact detection is done only using plurality of sensors in portable camera device 108, process 800 can start executing without any wireless connection is established. Process 800 begins at step 802 when a determination is made if an impact notification, indicating occurrence of impact, is received. If it is determined that an impact has occurred, then the processing proceeds to step 804, otherwise, the processing goes back to step 802. At step 804, the portable camera device 108 will capture the video image frames of the sports motion during the impact (starting from some time before the impact till some time after the impact). The process will then proceed to step 806 in which the captured video image will be saved in memory for future reference. The execution will then proceed back to step 802 where the portable camera device 108 will wait for occurrence of an impact.

In accordance with an embodiment of the present invention, the video capture system 108 includes at least one video recording device transmitting a video feed signal carrying video frame samples defining image information. The video cameras of the portable camera device 108 are positioned such that the front, side or rear view of a player is captured. The sports application 126 receives the video information signal and synchronizes the video information signal to the impact information signal.

In an embodiment, the image information signals coming from the camera 604 might be time-stamped using an internal clock mechanism.

In order to determine which video frame samples should be captured, a trigger event system is used by the sports application 126. The triggering event signal relates the occurrence of a trigger event, which provides the reference point in time, i.e., the trigger event time, that allows the sports application 126 to define a timing window for analysis. The timing window may be defined by a start time equal to the trigger event time minus a predetermined period, e.g., 3 seconds, and an end time equal to the trigger event time plus a predetermined period, e.g., 3 seconds. The data collected within the timing window is marked and stored for analysis and/or playback. If the collected data from the video camera 604 falls outside the timing window, then it is discarded out of the video capture buffers. The trigger event may be caused by impact between the sport equipment and a ball detected by the impact sensing device 106 mounted on the sport equipment or worn by the player.

Figure 9:
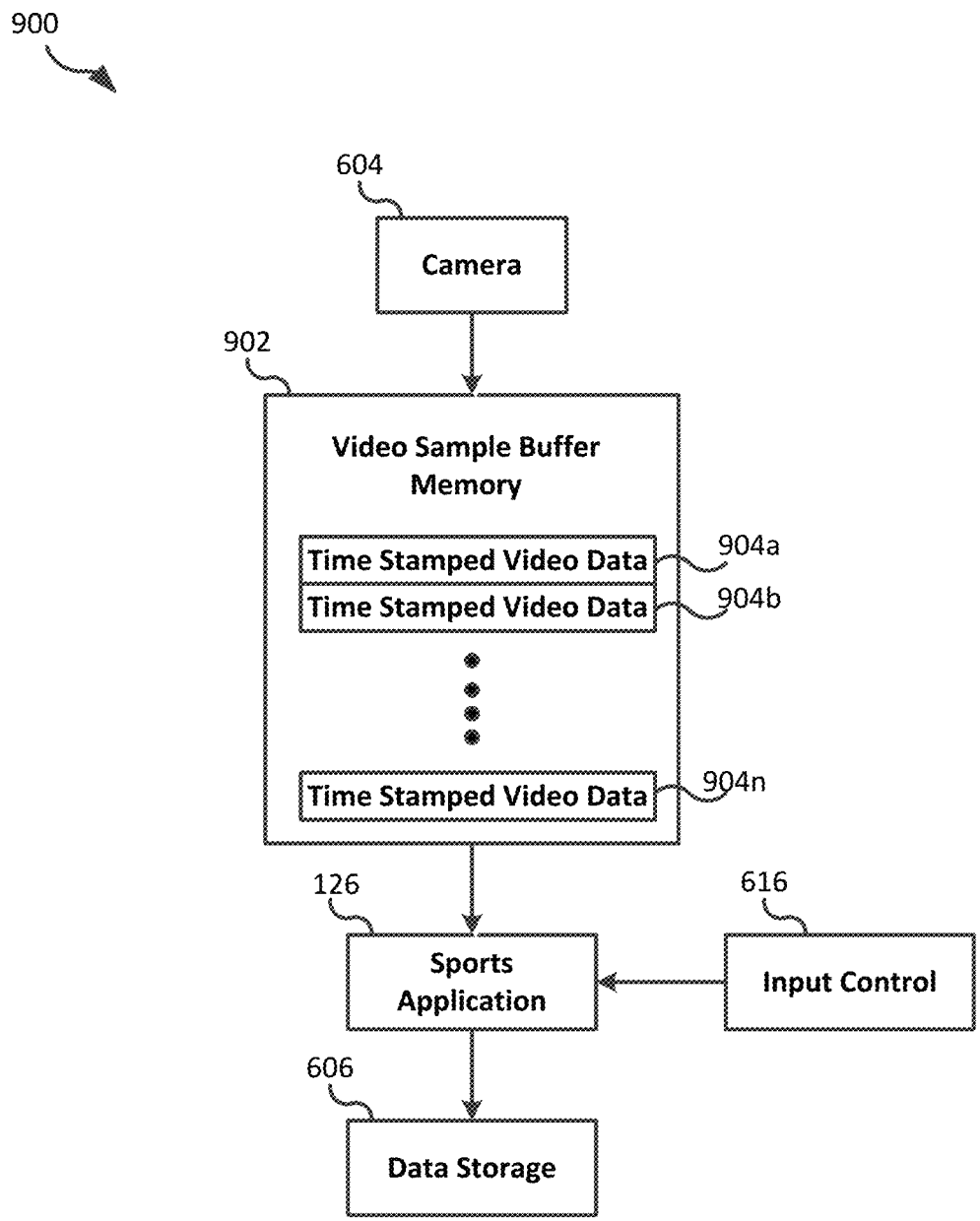
FIG. 9 illustrates an example embodiment of a video image capture methodology of the portable camera device.

FIG. 9 illustrates an example embodiment of a video image capture methodology of the portable camera device 108. In accordance with an embodiment of the present invention, the video image frame samples 904a-n received from camera 604 identified with the time stamp are stored in a video sample buffer memory 902. In accordance with an embodiment, the sample frame buffer 902 hold only the stamped video image frames 904 for a limited amount of time. The sample buffer 902 is preferably designed as first-in, first-out (FIFO) buffers. Accordingly, once the buffer memory 902 is full, earlier samples are erased as new samples are received by the buffer. Buffer memory 902 continue storing video image frames 904 until the time period defined by the timing window is expired. Once expired, the information is marked and stored to disk or another portion of memory 606 to be used during analysis.

In accordance with an embodiment, the sports application 126 continue collecting video frames 904 until the timing window expires. Continuation of the information collection by the sports application 126 ensure that information related to the follow-through swing of the player is collected. In an alternative embodiment, the sports application 126 may terminate video frame collection once a trigger event is sensed.

Upon completion of the trigger countdown, the video capture is stopped. Once the collection and compilation of data is completed, e.g., timing window completed, by the sports application 126, the stored video frame data samples 904 stored in the buffer 902 are converted to MPEG format and stored in permanent memory for later use.

In one embodiment of the invention, the sports application 126, may receive a measure of the impact force, between sport equipment and the ball, in the impact detection notification message sent by the impact detection device 106. In another embodiment of the invention, the sports application 126, may evaluate a measure of the impact force, between sport equipment and the ball based on the sensor signals received from plurality of impact sensors 620a and 620b. The sports application may store the impact force information for each stroke along with the corresponding recorded video for future reference.

Input control 616 is operably connected to the sport application module 126 and may be used to control the selection, operation, and appearance of analysis information in accordance with an embodiment of the present invention. For instance, the input control 616 may control the time duration of the capture window. If the player only wants stroke video displayed on the display 612, such a request is preferably made through the input control 616. Likewise, the input control 616 might allow the player or instructor to control a video playback of the sport swing. In accordance with another embodiment of the present invention, the input control 616 might be responsible for complete control of user selection, activation, operation, and termination of the sport application 126.

Figure 10:
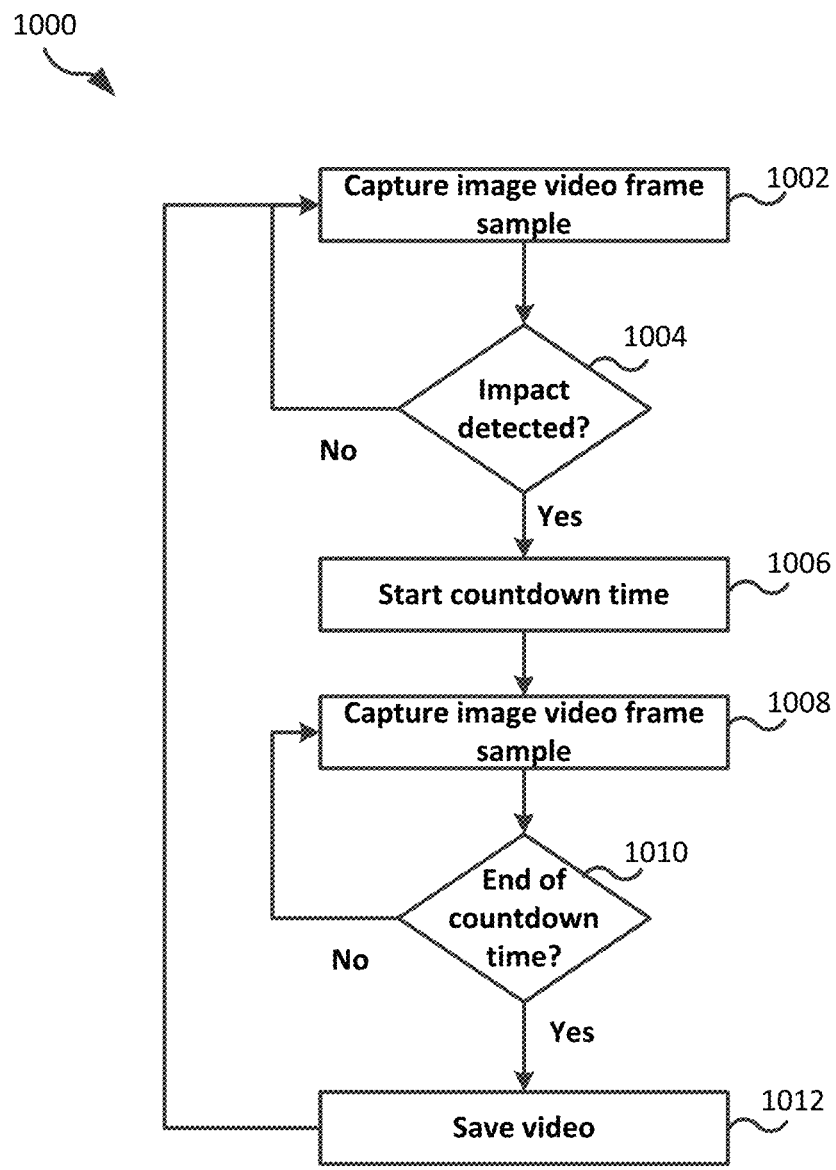
FIG. 10 illustrates an example flowchart of a process that may be performed by the sports application, running on the portable camera device, to capture a sport motion of a player using the impact detection notification from the impact detection device.

FIG. 10 illustrates an example flowchart 1000, according to an embodiment of the invention, of the said sports application 126 capturing a sport motion of a player using the impact detection notification from the impact detection device 106. The process 1000 begins at step 1002 where the sports application 126, capture a video frame and store the time stamped frame 904 in a buffer as detailed in FIG. 9. In accordance with an embodiment, the buffer 902 is a circular buffer having space for 120 video frames. In accordance with alternative embodiments, the circular buffer 902 may have space for any number of frames depending upon the desired length in time of the capture of a single swing or stroke. Data is stored in the buffer for a predetermined period of time so that if an impact is not detected in the predetermined time period, it will be overwritten since data in the buffer is stored in first in, first out basis. The operation flow will proceed to step 1004 where a determination is made whether an impact has been detected. If no notification is received, then the process will go back to step 1002 where the next frame will be captured, otherwise, it will proceed to step 1006. If the operation 1004 detects an impact event, then operation flow passes to step 1006 where a timing window is set to allow video frame data samples associated with the player's follow-through to be collected following detection of an impact. The process will then proceed to step 1008 where video frame capture will continue. At step 1010, a determination will be made if the countdown time has expired or not. If the predetermined countdown time has not expired, the process will go back to step 1008 where video frame capture will continue, otherwise, the flow will proceed to step 1012. In step 1012, the video frame capture process is terminated and the captured video frames 904 present in circular buffer 902 are stored in storage memory for later use in a format like JPEG or MPEG suitable for presentation to the player. The process 1000 will then go back to step 1002, where it will start capturing the video frames for the next stroke or swing.

In accordance with other embodiments, the predetermined countdown time period is set in step 1006 to a finite time period other than zero upon occurrence of impact event. In a specific embodiment, the predetermined time period is set by a countdown timer that counts video frame data samples. After 20 video frame data samples have been captured following an impact event, the video frame sample acquisition processes can be terminated. This specific configuration results in a 100-frame pre-trigger circular buffer.

According to one aspect of the invention, the individual videos for each captured swing motion can be put together in a single JPEG or MPEG file, which can be automatically uploaded by the sports application 126 running on portable camera device 108, to the Internet, for later retrieval at a remote site via the world wide web. The MPEG files may then be saved on a more permanent basis via a dedicated server. It should be noted that other formats and methods for capturing, storing and displaying video images may also be used, such as so-called streaming video.

According to one aspect of the invention, the sports application 126 may provide playback mode for adjustable speed and freeze-frame viewing, as well as side-by-side comparison with prior swings of the player or with pre-saved 'professional' swings. According to another aspect of the invention, the impact force measurement can be displayed on the monitor screen alongside an instant replay of the swing to enable the user to accurately gauge and measure performance.

Figure 11:
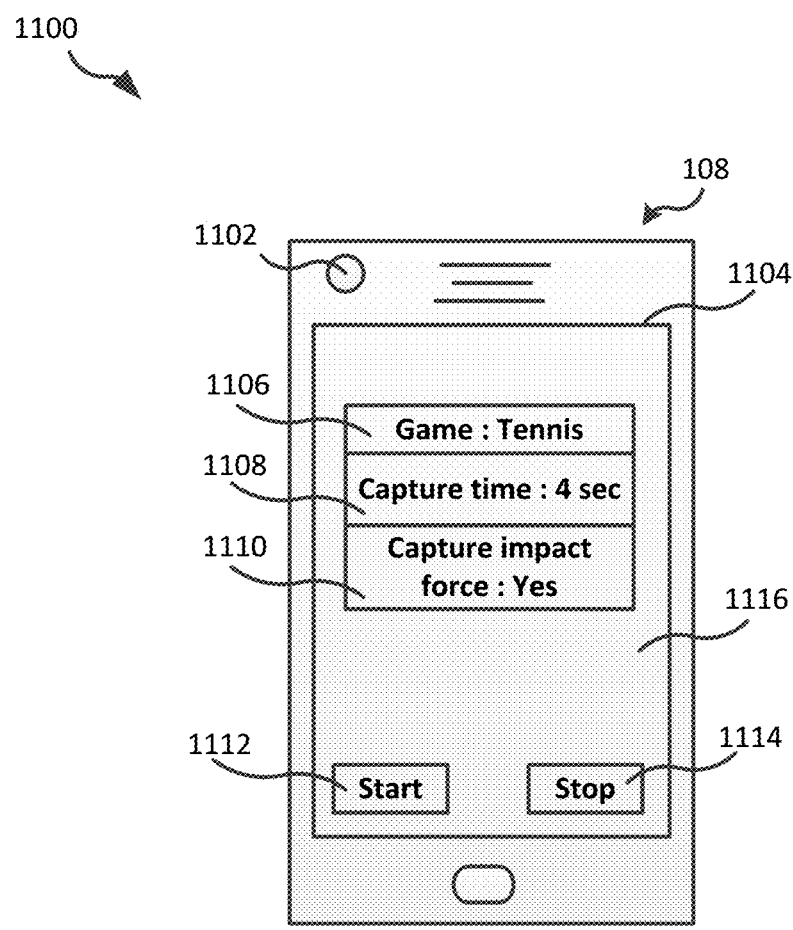
FIG. 11 illustrates example features that may be provided in and/or controlled by graphical user interfaces of portable camera device in accordance with an example embodiment of this invention.

FIG. 11 shows an example of a portable camera device 108 with a display screen 1104 having an example user interface 1116, presented by the sports application 126, allowing user input of information relating to user specific settings. This example interface 1116 includes a panel 1106 through which the name of the game whose sport motion needs to be captured, may be selected from a listing and another panel 1108 through which the time duration of the capture window may be entered and another panel 1110 through which the through which the option for capturing the force of impact can be selected. In addition, this user interface 1116 includes "start" button 1112 and "stop" button 1114 that allow users to either start or stop capturing the video image of the sport motion. The sports application 126 will take the user inputs and execute accordingly. The user selecting the "start" option, for example, may trigger the sports application 126, to establish a wireless link with the impact detection device 106. According to one aspect of the invention, the sports application will send some of the configuration parameters to the impact detection device 106. According to another embodiment of the invention, the user selecting the "start" option, may trigger the sports application 126, to start receiving signals from one or more impact sensors in portable camera device 108.

Figure 12:
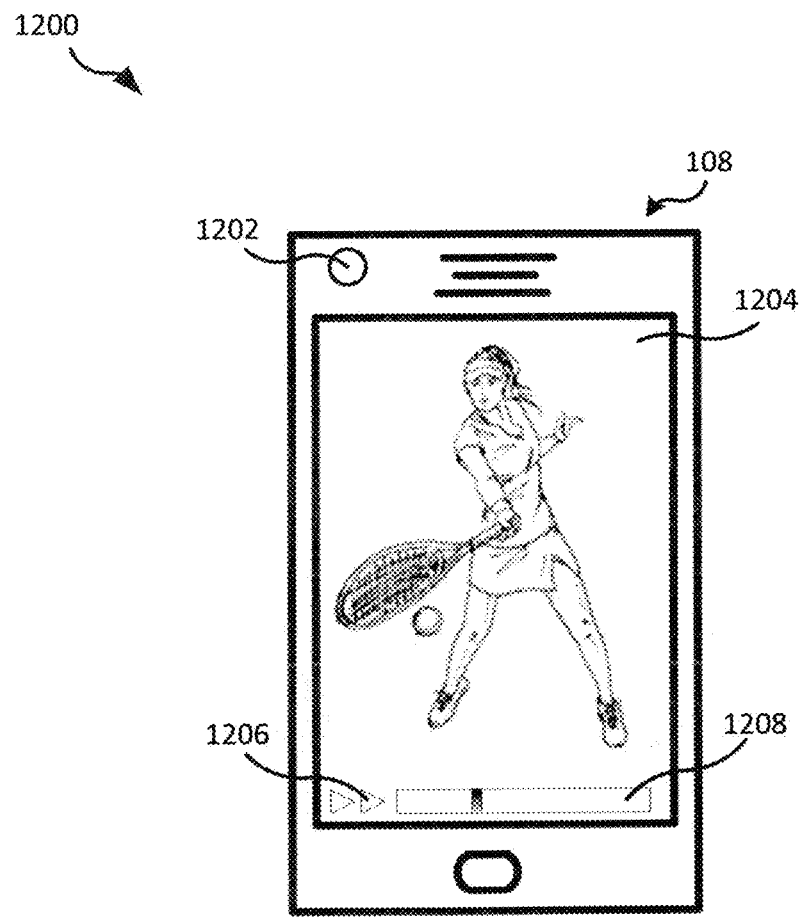
FIG. 12 illustrates an example portable camera device displaying recorded video image of a sport motion.

FIG. 12 illustrates an example portable camera device 108, a smart phone, having a camera 1202, a display and touch screen 1204, playing a recorded video of a tennis stroke. The video playback mode like slow motion, pause and the like can be controlled by user interface control 1206. 1208 is the video playback progress bar.

Figure 13A:
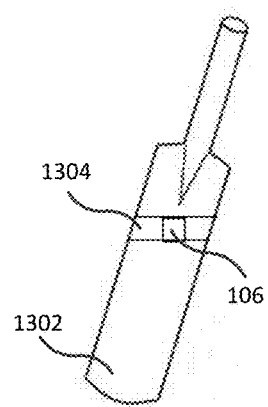
FIGS. 13A and 13B is an illustration of a strap, with integrated impact detection device, attached to a sport equipment and wrist of a player according to an embodiment of the present invention.
Figure 13B:
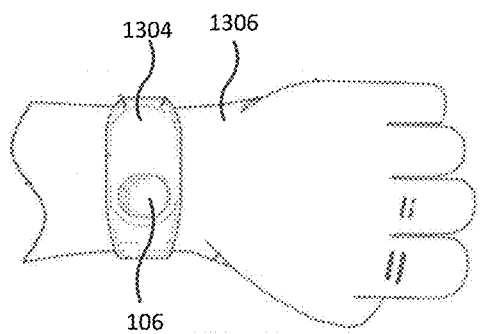

FIG. 13A-B illustrates an embodiment of the invention in which the impact detection device 106 is attached to the sport equipment and to the wrist using a strap. In an embodiment of the invention, the impact detection device 106 may be integrally and fixedly incorporated into or releasably attached to a sport equipment 1302. In another embodiment, the impact detection device 106 may be integrally and fixedly incorporated into or releasably attached to a strap 1302 to be put on the sport equipment 1302 or player's wrist 1306.

With reference to FIGS. 13A and 13B, the universal interface 316 is depicted as a strap 1304 releasably secured to the sport equipment 1302 or wrist of the player 1306.

Figure 14:
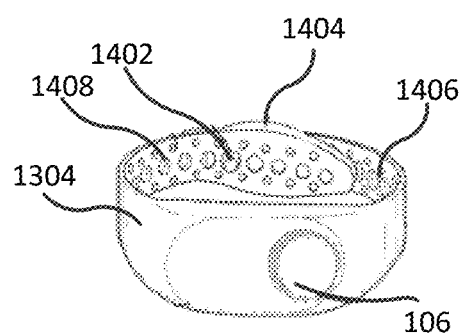
FIG. 14 is a front elevational view of a strap, with integrated impact detection device, according to an embodiment of the present invention.

FIG. 14 is an illustration of an universal interface 316 in the form of a strap 1304 according to one embodiment of the present invention. The strap 1304 is adapted to be releasably secured to the sport equipment or wrist or clothing of a player. The strap 1304 may be flexible to fit around the sport equipment or player's wrist, and may have a central portion between first and second end portions. In one embodiment, the strap 1304 may be molded out of a flexible polymeric material, such as, for example, polyurethane. Other materials, including, but not limited to, rubber, plastic, TPU, cloth, leather, PU, silicon, metal, and/or other suitably flexible materials may be used. In one embodiment, the strap 1304 may be injection molded. Flexible straps 1304 may be formed from inflexible materials such as, for example, a plurality of small metal rings or pieces linked together to form a mesh-like strap. More traditional metallic straps such as those commonly employed in wrist watches that are comprised of a series of interconnected members may also be employed. Other suitable manufacturing techniques may be used.

The strap 1304 may include fastening means 1402 for releasably securing the strap 1304 around the sport equipment or wrist. In one embodiment, a fastener 1402 may have one or more male and female components for securing the strap 1402 around the sport equipment like 1302 or wrist 1306. The components of the fastener 1402 may be injection molded and integrally formed with the strap 1304, or they may be separate components. Multiple female components may be provided along the length of strap 1304 so that the strap 1304 is adaptable to varying sport equipment and wrist sizes. One or more male components may be provided to engage with one or more of the female components. The strap 1304 may additionally include ridges 1404 to keep any overlapping first and second end portions of the strap 1304 in a relatively parallel configuration. The inner surface 1406 of the strap 1304 may include dimples and/or protuberances 1408 or other surface characteristics to limit relative motion between the inner surface 1406 of the strap 1304 and the sport equipment 1302 or player's wrist 1306.

Other fastening means 1402 may be used to releasably secure the strap 1304 around the sport equipment 1302 or wrist 1306, including, but not limited to, hook and loop fasteners (e.g., VELCRO®), snaps, buttons, buckles, clasps, magnets, or other suitable means. In one embodiment, the strap 1304 may not include fastening means 1402. In this embodiment, the strap may be made of a suitably elastic material such that the strap 1304 may remain releasably secured around the sport equipment 1302 or wrist 1306 without fastening means. In another embodiment, the strap 1304 may be a continuous loop racking first and second ends. The continuous loop strap 1304 may be made of a suitably elastic material such that the strap 1304 may stretch to pass over the sport equipment 1302 or player's hand and thereafter contract to remain releasably secured around the sport equipment or player's wrist 1306.

Figure 15:
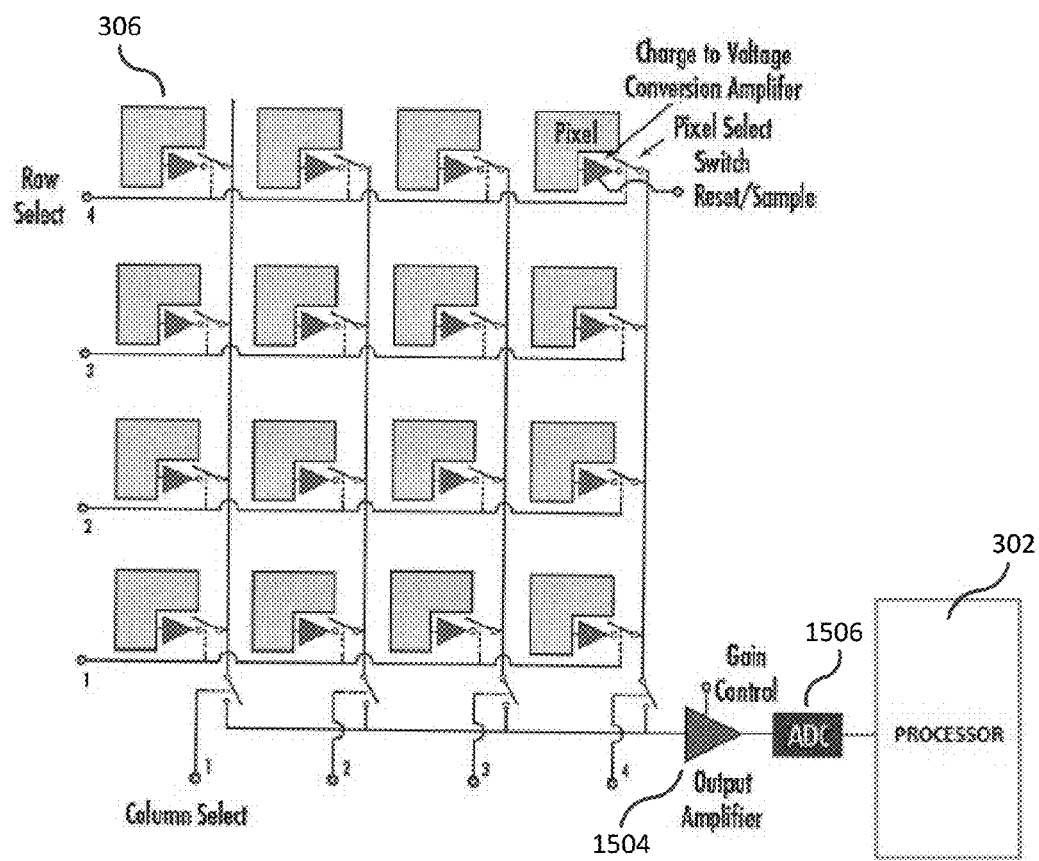
FIG. 15 is an example circuit diagram of an image sensor used for impact detection.

FIG. 15 shows an example of a circuit which can be employed to detect the occurrence of impact and measure the impact force. The sensor circuit shown in FIG. 15 are the core components of a CMOS image sensor which provides an output signal that is a voltage proportional to the image. The sensor element 306 is connected to the processor 302. The conditioning electronics 312 comprises of charge amplifier 1504 and analog to digital converter 1506. The charge from the photosensitive pixel is converted to a voltage at the pixel site and the signal is multiplexed by row and column to multiple on-chip analog-to-digital converters (ADC). Each pixel can be photodiode, photocapacitor or the like, which generate a charge proportional to the amount of light incident on that discrete place of the sensor.

Those skilled in the art should appreciate that changes can be made within the description above without departing from the scope of the invention.

The invention thus attains the objects set forth above, among those apparent from preceding description. Since certain changes may be made in the above apparatus and methods without departing from the scope of the invention, it is intended that all matter contained in the above description or shown in the accompanying drawing be interpreted as illustrative and not in a limiting sense.

What is claimed is:

1. A system for detecting impact comprising:
   at least one impact sensor producing electrical signal;
   a monitoring circuit;
   a processor that performs functions comprising:
      receiving the electrical signal and processing the electrical signal from the at least one impact sensor;
      generating impact detection notification;
   wherein the monitoring circuit comprises:
      at least one analog to digital converter to translate the electrical signal provided by the at least one impact sensor into a digital signal;
   wherein the impact is detected by determining signal to noise ratio of input data provided by the at least one analog to digital converter exceeding an impact detection threshold, wherein the impact detection threshold of the signal to noise ratio of the at least one impact sensor is user configurable.

2. The system of claim 1, wherein the impact detection notification further comprises of impact notification data.

3. The system of claim 1, wherein the processor further performs a function of running signal processing algorithms.

4. The system of claim 2, wherein the impact notification data includes at least one element selected from a group comprising:
   time of impact;
   impact related information.

5. The system of claim 4, wherein the impact related information includes at least one element selected from a group comprising:
   amplitude of the impact;
   the signal to noise ratio of the sensor signal generated from the impact.

6. The system of claim 2, wherein the processor further operates on the impact notification data to generate a performance value comprising:
   force value;
   speed;
   acceleration.

7. The system of claim 1, wherein the signal to noise ratio is determined by,
   obtaining the signal which is an output of a moving average filter of an absolute value of an incoming signal whose absolute value exceeds a pre-determined threshold;
   obtaining a noise which is an output of the moving average filter of the incoming signal whose absolute value is below a pre-determined threshold;
   dividing the signal by the noise.

8. The system of claim 1, wherein the monitoring circuit further comprises of at least one signal processing filter.

9. The system of claim 1, wherein the at least one impact sensor is user selectable.

10. The system of claim 1, wherein the at least one impact sensor is communicatively connected by wires to the processor.

11. The system of claim 1, wherein the at least one impact sensor is communicatively connected by wireless signals to the processor.

12. The system of claim 1, wherein the impact sensor is selected from a group comprising:
   motion sensor;
   piezo-electric sensor;
   sound sensor.

13. The system of claim 12, wherein the motion sensor is selected from a group comprising:
   accelerometer;
   rate gyroscope;
   magnetometer;
   infrared sensor;
   image sensor.

14. The system of claim 2, further comprising an image recording system comprising at least one camera wherein, the processor further performs one or more functions from a group comprising:
  receiving video from the camera;
  receiving still images from the camera;
  saving the video in slow motion or normal speed;
  concatenating a plurality of the video to make a single video for purposes of review, comment and sharing;
  saving the video in local memory or on a server;
  saving the still images in local memory or on a server;
  saving the impact notification data along with the video;
  saving the impact notification data along with the still images;
  executing an application program to allow interaction with the camera and the at least one impact sensor.

15. The system of claim 14, wherein the image recording system upon receiving impact detection notification records the video around the time of impact.

16. The system of claim 15, wherein the duration of the video taken before the time of impact is user configurable.

17. The system of claim 15, wherein the duration of the video taken after the time of impact is user configurable.

18. The system of claim 14, wherein the image recording system records the video at a user configurable video frame rate.

19. The system of claim 15, wherein the impact related information is saved along with the corresponding saved video.

20. The system of claim 14, wherein the image recording system upon receiving impact detection notification captures the still image at a plurality of user configurable predetermined times around the time of impact.

21. The system of claim 20, wherein impact related information is saved along with the still images.

22. The system of claim 14, wherein the application program running on the processor provides a user interface to execute at least one function from a group comprising:
  start and stop the video recording;
  review the captured videos;
  review the captured videos along with impact related information;
  add comments after reviewing the video;
  edit and save snippets of the captured video;
  compare the videos;
  configure parts of the video to be shown in slow motion to allow detailed review of a user action;
  edit and save the captured still images;
  review the captured still images;
  review the captured still images along with impact related information;
  compare the still images;
  configure the video frame rate;
  configure whether to take the still images in addition to the video;
  configure length of the video capture;
  configure plurality of times when the still image is taken.

* * * * *